United States Patent
Kuramoto et al.

(10) Patent No.: US 9,423,320 B2
(45) Date of Patent: Aug. 23, 2016

(54) TIRE RUBBER INDEX CALCULATING METHOD, DEVICE, AND COMPUTER-READABLE STORAGE MEDIUM

(75) Inventors: Yusuke Kuramoto, Kodaira (JP); Tomonori Shibata, Kodaira (JP)

(73) Assignee: BRIDGESTONE CORPORATION, Tokyo (JP)

( * ) Notice: Subject to any disclaimer, the term of this patent is extended or adjusted under 35 U.S.C. 154(b) by 813 days.

(21) Appl. No.: 13/391,999

(22) PCT Filed: Aug. 25, 2010

(86) PCT No.: PCT/JP2010/064423
§ 371 (c)(1),
(2), (4) Date: Apr. 17, 2012

(87) PCT Pub. No.: WO2011/024877
PCT Pub. Date: Mar. 3, 2011

(65) Prior Publication Data
US 2012/0197548 A1 Aug. 2, 2012

(30) Foreign Application Priority Data
Aug. 25, 2009 (JP) ................................. 2009-194161

(51) Int. Cl.
*G01B 3/44* (2006.01)
*G01M 17/02* (2006.01)
(Continued)

(52) U.S. Cl.
CPC ............... *G01M 17/02* (2013.01); *B60C 11/24* (2013.01); *B60C 11/246* (2013.04); *B60C 99/006* (2013.04); *G01N 19/02* (2013.01); *B60T 2210/12* (2013.01)

(58) Field of Classification Search
USPC .......................................................... 702/34
See application file for complete search history.

(56) References Cited

U.S. PATENT DOCUMENTS 6,212,947 B1 * 4/2001 Shimizu et al. .................. 73/146
6,263,728 B1 7/2001 Sumiya et al.
(Continued)

FOREIGN PATENT DOCUMENTS

EP 0969276 A2 1/2000
JP 11-326144 A 11/1999
(Continued)

OTHER PUBLICATIONS
International Search Report for PCT/JP2010/064423 dated Nov. 2, 2010.

*Primary Examiner* — Paul D Lee
(74) *Attorney, Agent, or Firm* — Sughrue Mion, PLLC

(57) ABSTRACT

In order to precisely calculate the rubber index of a tire, a rubber index calculating device: measures, by a frictional energy measuring device, frictional energies of a tire in plural tire input conditions applied to the tire on the basis of the shear force and the slippage of a tire contact patch; measures, by the frictional energy measuring device, frictional energies of a sample of the same material as the tire in sample input conditions that have been set on the basis of the frictional energies of the tire in the tire input conditions that were measured, and sets measurement conditions for measuring amounts of wear of the sample on the basis of the frictional energies of the tire in the tire input conditions that were measured and the frictional energies of the sample in the tire input conditions that were measured; measures, by an amount of wear measuring device, the amounts of wear of the sample in the measurement conditions that were set, and calculates the rubber index of the tire on the basis of the frictional energies and the amounts of wear of the sample that were measured.

6 Claims, 11 Drawing Sheets

(51) Int. Cl.
  *B60C 11/24* (2006.01)
  *G01N 19/02* (2006.01)
  *B60C 99/00* (2006.01)

(56) References Cited

U.S. PATENT DOCUMENTS

| | | | |
|---|---|---|---|
| 6,269,690 | B1 | 8/2001 | Shimizu et al. |
| 2008/0228411 | A1 | 9/2008 | Miyashita et al. |

FOREIGN PATENT DOCUMENTS

| | | |
|---|---|---|
| JP | 2001-47822 A | 2/2001 |
| JP | 3277155 B2 | 4/2002 |
| JP | 2003-50190 A | 2/2003 |
| JP | 3406643 B2 | 5/2003 |
| JP | 2006-232011 A | 9/2006 |
| JP | 2006-242697 A | 9/2006 |
| JP | 2008-82914 A | 4/2008 |

* cited by examiner

TIRE RUBBER INDEX CALCULATING METHOD, DEVICE, AND COMPUTER-READABLE STORAGE MEDIUM

CROSS REFERENCE TO RELATED APPLICATIONS

This application is a National Stage of International Application No. PCT/JP2010/064423, filed on Aug. 25, 2010, which claims priority from Japanese Patent Application No. 2009-194161 filed on Aug. 25, 2009, the contents of all of which are incorporated herein by reference in their entirety.

TECHNICAL FIELD

The present invention pertains to a tire rubber index calculating method, device, and computer-readable storage medium, and particularly relates to a rubber index calculating method, device, and computer-readable storage medium that calculate the rubber index of a tire such as a pneumatic tire used in automobiles and so forth.

BACKGROUND ART

Conventionally, as a method of predicting the wear of a tire such as a pneumatic tire used in automobiles and so forth, in Japanese Patent No. 3,277,155 for example, there is disclosed a technology that measures the amount of wear and the frictional energy of a tire and predicts the wear of the tire with a rubber index that is determined on the basis of these.

Further, as a device that measures frictional energy, in Japanese Patent No. 3,277,155 and Japanese Patent No. 3,406,643 for example, there are disclosed contact portion measuring devices for tire contact patches that apply a marking to a tire, image the tire contact patch with a camera, measure the shear force and the slippage of the tire contact patch on the basis of the image, and measure the frictional energy.

Further, in Japanese Patent No. 3,277,155 and Japanese Patent Application Laid-Open (JP-A) No. 2006-242697, there are disclosed Lambourne testing devices that measure, with the so-called Lambourne test, the wear of a sample (test piece) of rubber used in a tread portion of a tire.

Further, in JP-A No. 2003-50190, there is disclosed a device that measures the amount of wear of a tire with a drum wear test.

DISCLOSURE OF INVENTION

Technical Problem

In order to measure the wear of a tire, precisely finding the rubber index determined from the amount of wear and the frictional energy of the tire becomes important, but the Lambourne test measures the amount of wear of a sample by pushing a sample of a tire against a grinding drum and causing it to rotate, and the Lambourne test cannot measure frictional energy. For this reason, in the case of calculating frictional energy, frictional energy has been calculated as a frictional energy that has been averaged on the basis of the axial force applied to the sample and the slippage. The axial force in this case is, as shown in FIGS. 7 and 8, found by the sum of the total sum of the force (driving force) on the contact front end and the total sum of the force (braking force) on the contact rear end, but the direction in which the driving force is generated and the direction in which the braking force is generated are opposite directions, so in a case where the absolute value of the total sum of the driving force and the absolute value of the total sum of the braking force are the same, the sum of the total sum of the driving force and the total sum of the braking force becomes zero, and there are cases where the axial force ends up becoming zero. Because of this, there are cases where the frictional energy ends up becoming zero.

However, in actuality, as shown in FIG. 9, in the neighborhood of the contact rear end of the tire, there exists a region in which the tire wears, and particularly in a region where the frictional energy is low, if the frictional energy is calculated on the basis of the axial force, an averaged frictional energy ends up being calculated, so the frictional energy cannot be precisely found. Consequently, it is necessary to find the frictional energy on the basis of the shear force rather than finding the frictional energy on the basis of the axial force.

Devices that measure the frictional energy on the basis of the shear force are described in Japanese Patent No. 3,277,155 and Japanese Patent No. 3,406,643 as mentioned above, and a method that uses these devices to measure the frictional energy and uses the drum wear testing device described in JP-A No. 2003-50190 to measure the amount of wear of the tire and calculate the rubber index is also conceivable, but these devices measure the shear force and the slippage of the tire contact patch of an actual tire rather than a sample and measure the frictional energy and measure the amount of wear. For this reason, they have excellent measurement precision, but they have had the problem that they require a long time for measurement preparation and actual measurement and costs become higher. In order to solve this problem, a method of making and measuring a miniature-sized tire is also conceivable but is not realistic because manufacturing a miniature-sized tire also requires high manufacturing precision.

In consideration of the above-described circumstances, it is an object of the present invention to obtain a tire rubber index calculating method, device, and computer-readable storage medium that can precisely calculate the rubber index of a tire such as a pneumatic tire used in automobiles and so forth.

Solution to Problem

In order to achieve the above-described object, a tire rubber index calculating method pertaining to the first aspect of the present invention includes: a tire frictional energy measuring step of measuring, by a frictional energy measuring device, tire frictional energies of a tire in plural tire input conditions applied to the tire on the basis of the shear force and the slippage of a tire contact patch; a setting step of obtaining sample frictional energies of a sample of the same material as the tire in sample input conditions that have been set on the basis of the tire frictional energies in the tire input conditions that were measured, and setting measurement conditions for measuring sample amounts of wear of the sample on the basis of the tire frictional energies in the tire input conditions that were measured and the sample frictional energies that were obtained for the sample input conditions; a sample amount of wear measuring step of measuring, by an amount of wear measuring device, the sample amounts of wear of the sample in the measurement conditions that were set; and a rubber index calculating step of calculating a rubber index of the tire on the basis of the sample frictional energies and the sample amounts of wear that were measured.

According to this invention, the tire rubber index calculating method measures, by the frictional energy measuring device that measures the frictional energy of the sample on the basis of the shear force and the slippage of the tire contact patch, the amount of wear of the sample in the measurement conditioned that has been set on the basis of the frictional energy of the sample that was measured and the frictional energy of the tire, and calculates the rubber index. For this reason, compared to the case of calculating a frictional energy that has been averaged on the basis of the axial force like conventionally, the frictional energy can be measured precisely and the rubber index can be calculated precisely.

According to the second aspect of the present invention, the tire rubber index calculating method may be configured in such a way that the setting step includes, a step of calculating, per type of the tire input conditions, frictional energy functions representing the correspondence relationships between the tire input conditions and the tire frictional energies, a step of calculating expected values of the tire frictional energies on the basis of frequency data representing the relationships between tire inputs that were measured in actual vehicle travel using the tire and the frequencies of the tire inputs and the frictional energy functions per type of the tire input conditions, a sample input condition setting step of setting a sample input condition applied to the sample for measuring, by the frictional energy measuring device, the sample frictional energy of the sample, a sample frictional energy measuring step of measuring the sample frictional energy of the sample in the sample input condition that was set and measuring the sample frictional energy while changing the sample input condition until the sample frictional energy that has been measured matches the expected value of the tire frictional energy, and a sample amount of wear measurement condition setting step of setting, as a measurement condition for measuring the sample amount of wear, the sample input condition in which the sample frictional energy that was measured matches the expected value of the tire frictional energy, wherein the sample amount of wear measuring step includes measuring the sample amount of wear of the sample in the measurement condition that was set in the sample amount of wear measurement condition setting step.

Further, according to the third aspect of the present invention, the tire rubber index calculating method may be configured in such a way that the setting step includes in regard to each of the plural tire input conditions, a sample input condition setting step of setting a sample input condition applied to the sample for measuring, by the frictional energy measuring device, the sample frictional energy of the sample, a sample frictional energy measuring step of measuring the sample frictional energy of the sample in the sample input condition that was set and measuring the sample frictional energy while changing the sample input condition until the sample frictional energy that has been measured matches the tire frictional energy that was measured in the corresponding tire input condition, and a sample amount of wear measurement condition setting step of setting, as a measurement condition for measuring the sample amount of wear, the sample input condition in which the sample frictional energy that was measured matches the tire frictional energy that was measured in the corresponding tire input condition, wherein the sample amount of wear measuring step comprises measuring the sample amounts of wear of the sample in the measurement conditions that were set in the sample amount of wear measurement condition setting step in regard to each of the plural tire input conditions, and the rubber index calculating step includes a step of calculating rubber indexes on the basis of the frictional energies and the sample amounts of wear in regard to each of the plural tire input conditions, a step of calculating, per type of the tire input conditions, rubber index functions representing the correspondence relationships between the tire input conditions and the rubber indexes of the tire on the basis of the rubber indexes that were calculated in regard to each of the plural tire input conditions, and a step of calculating expected values of the rubber indexes on the basis of frequency data representing the relationships between tire inputs that were measured in actual vehicle travel using the tire and the frequencies of those tire inputs and the rubber index functions per type of the tire input conditions.

Further, according to the fourth aspect of the present invention, the tire rubber index calculating method may be configured in such a way that the setting step includes a step of calculating, per type of the tire input conditions, frictional energy functions representing the correspondence relationships between the tire input conditions and the tire frictional energies, a step of calculating expected values of the tire frictional energies on the basis of frequency data representing the relationships between tire inputs that were measured in actual vehicle travel using the tire and the frequencies of those tire inputs and the frictional energy functions per type of the tire input conditions, a sample input condition setting step of setting a sample input condition applied to the sample for computing the sample frictional energy of the sample on the basis of a sample model of the sample, a sample frictional energy computing step of computing the sample frictional energy of the sample in the sample input condition that was set and computing the sample frictional energy while changing the sample input condition until the sample frictional energy that has been computed matches the expected value of the tire frictional energy, and a sample amount of wear measurement condition setting step of setting, as a measurement condition for measuring the sample amount of wear, the sample input condition in which the sample frictional energy that was computed matches the expected value of the tire frictional energy, wherein the sample amount of wear measuring step includes measuring the sample amount of wear of the sample in the measurement condition that was set in the sample amount of wear measurement condition setting step.

Further, according to the fifth aspect of the present invention, the tire rubber index calculating method may be configured in such a way that the setting step includes in regard to each of the plural tire input conditions, a sample input condition setting step of setting a sample input condition applied to the sample for computing the sample frictional energy of the sample on the basis of a sample model of the sample, a sample frictional energy computing step of computing the sample frictional energy of the sample in the sample input condition that was set and computing the sample frictional energy while changing the sample input condition until the sample frictional energy that has been computed matches the tire frictional energy that was measured in the corresponding tire input condition, and a sample amount of wear measurement condition setting step of setting, as a measurement condition for measuring the sample amount of wear, the sample input condition in which the sample frictional energy that was computed matches the tire frictional energy that was measured in the corresponding tire input condition, wherein the sample amount of wear measuring step includes measuring the sample amounts of wear of the sample in the measurement conditions that were set in the sample amount of wear measurement condition setting step in regard to each of the plural tire input conditions, and the rubber index calculating step includes a step of calculating rubber indexes on the basis of the frictional energies and the sample amounts of wear in regard to each of the plural tire input conditions, a step of calculating, per type of the tire input conditions, rubber index functions representing the correspondence relationships between the tire input conditions and the rubber indexes of the tire on the basis of the rubber indexes that were calculated in regard to each of the plural tire input conditions, and a step of calculating expected values of the rubber indexes on the basis of frequency data representing the relationships between tire inputs that were measured in actual vehicle travel using the tire and the frequencies of those tire inputs and the rubber index functions per type of the tire input conditions.

The tire rubber index calculating method can be easily realized by the following device. Specifically, a tire rubber index calculating device according to the sixth aspect of the present invention includes: tire frictional energy measuring unit that measures, by a frictional energy measuring device, tire frictional energies in plural tire input conditions applied to the tire on the basis of the shear force and the slippage of a tire contact patch; setting unit that obtains sample frictional energies of a sample of the same material as the tire in sample input conditions that have been set on the basis of the tire frictional energies in the tire input conditions that were measured, and setting measurement conditions for measuring sample amounts of wear of the sample on the basis of the tire frictional energies in the tire input conditions that were measured and the sample frictional energies that were obtained in the sample input conditions; sample amount of wear measuring unit that measures, by an amount of wear measuring device, the sample amounts of wear of the sample in the measurement conditions that were set; and rubber index calculating unit that calculates a rubber index of the tire on the basis of the sample frictional energies and the sample amounts of wear that were measured.

Further, in the case of calculating the rubber index of a tire with a computer, according to the seventh aspect of the present invention, the computer may be caused to execute a tire rubber index calculating process including: a tire frictional energy measuring step of measuring, by a frictional energy measuring device, tire frictional energies of a tire in plural tire input conditions applied to the tire on the basis of the shear force and the slippage of a tire contact patch; a setting step of obtaining sample frictional energies of a sample of the same material as the tire in sample input conditions that have been set on the basis of the tire frictional energies in the tire input conditions that were measured, and setting measurement conditions for measuring sample amounts of wear of the sample on the basis of the tire frictional energies in the tire input conditions that were measured and the sample frictional energies that were obtained in the sample input conditions; a sample amount of wear measuring step of measuring, by an amount of wear measuring device, the sample amounts of wear of the sample in the measurement conditions that were set; and a rubber index calculating step of calculating a rubber index of the tire on the basis of the sample frictional energies and the sample amounts of wear that were measured.

Advantageous Effects of Invention

As described above, according to the present invention, the present invention has the effect that it can precisely calculate the rubber index of a tire such as a pneumatic tire used in automobiles and so forth.

BEST MODES FOR CARRYING OUT THE INVENTION

First Embodiment

Figure 1:
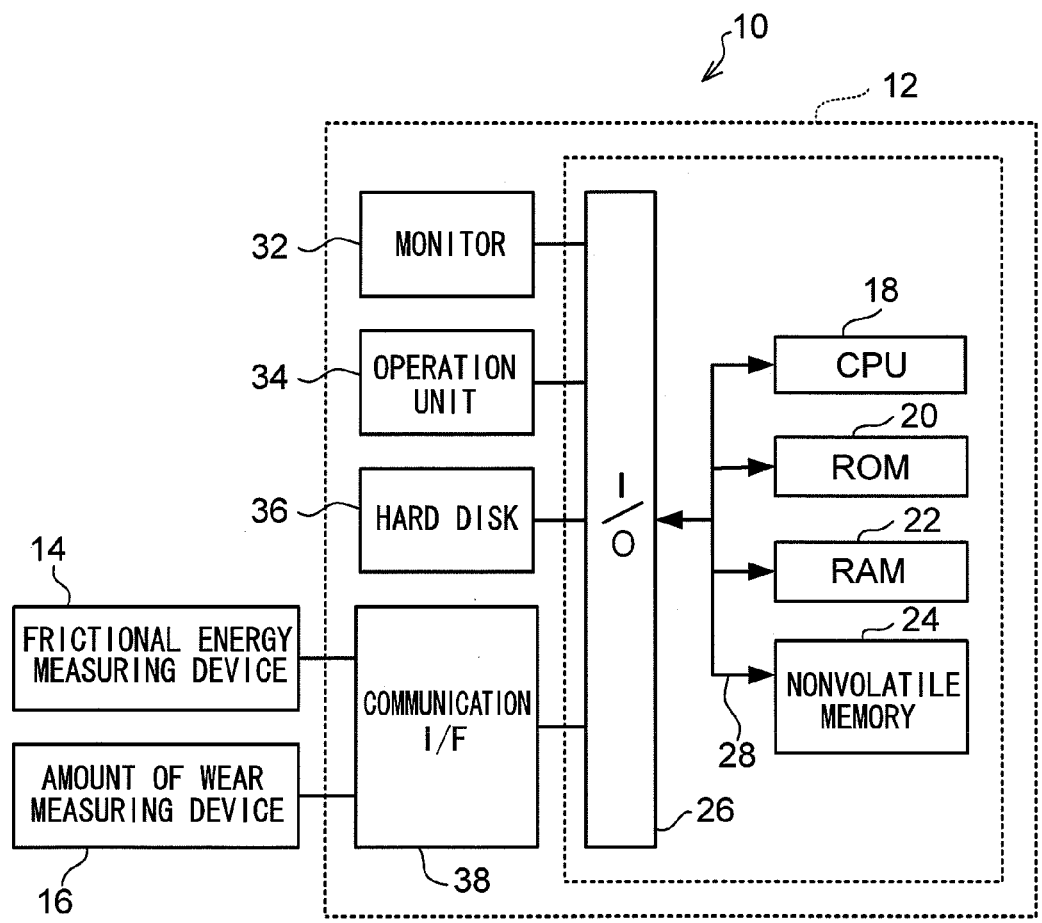
FIG. 1 is a schematic configuration diagram of a rubber index calculating system.

FIG. 1 shows a tire rubber index calculating system 10 pertaining to the present embodiment. As shown in the same figure, the tire rubber index calculating system 10 is configured to include a tire rubber index calculating device 12, a frictional energy measuring device 14, and an amount of wear measuring device 16.

The tire rubber index calculating device 12 is, as shown in FIG. 1, configured to include a computer in which a CPU (Central Processing Unit) 18, a ROM (Read Only Memory) 20, a RAM (Random Access Memory) 22, a nonvolatile memory 24, and an input/output interface (I/O) 26 are interconnected via a bus 28.

A monitor 32 configured by a liquid crystal display or the like, an operation unit 34 configured by a keyboard and a mouse or the like, a hard disk 36, and a communication interface (I/F) 38 are connected to the I/O 26. The frictional energy measuring device 14 and the amount of wear measuring device 16 are connected to the communication OF 38.

The frictional energy measuring device 14 measures the frictional energy of a contact patch of, for example, a disc-shaped sample of the same material as the tread portion of a tire whose rubber index is to be calculated, for example. As this device, for example, the contact portion measuring devices for tire contact patches described in Japanese Patent No. 3,277,155 and Japanese Patent No. 3,406,643 mentioned above can be used. In the present embodiment, the frictional energy measuring device 14 measures the frictional energy of the contact patch of the sample, whose size is significantly smaller than that of the tire, and not the tire itself, so it is preferred that the resolution of the camera that images the contact patch of the sample and the sampling rate of the imaging be made higher than in the case of measuring the frictional energy of the contact patch of the tire.

Figure 2A:
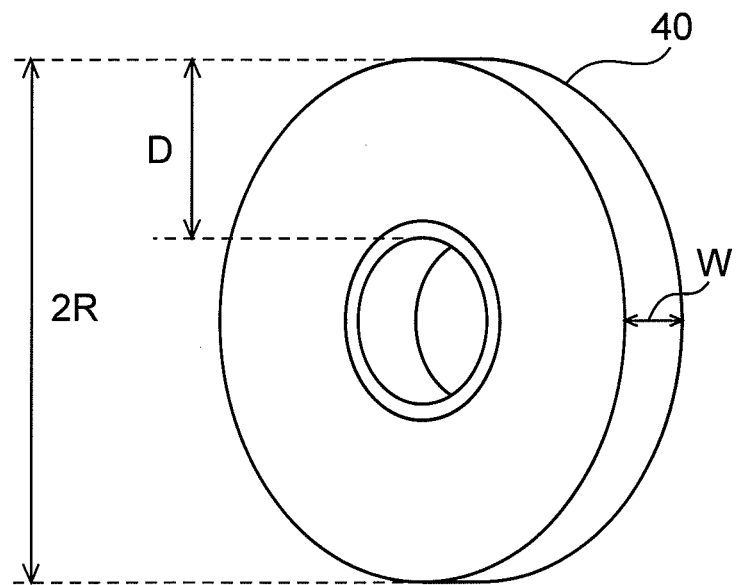
FIG. 2A is a perspective view showing an example of a sample.
Figure 2B:
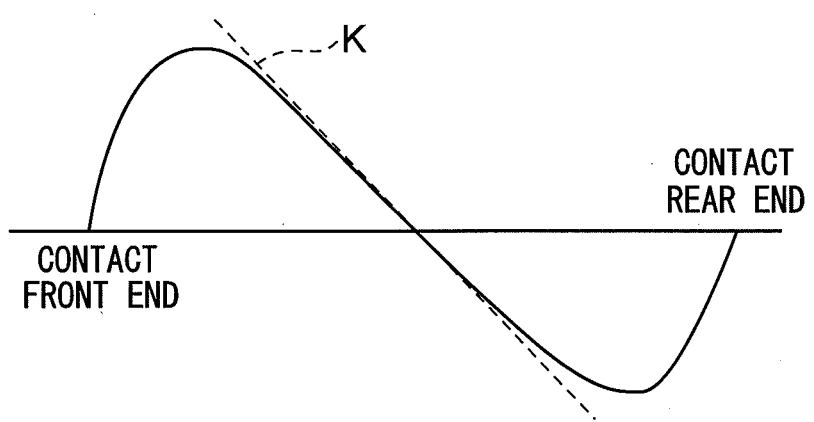
FIG. 2B is a diagram showing the characteristic of a shear force of the sample.

As the sample, a sample 40 such as shown in FIG. 2A, for example, is used. In this case, it is preferred that its width W be equal to or greater than 5 mm, its diameter 2R be less than 80 mm, and its thickness (from the outer diameter to the inner diameter of the sample 40) D be equal to or greater than 5 mm. Further, as shown in FIG. 2B, it is preferred that a sample in which the slope K of the shear force becomes negative be used.

The amount of wear measuring device 16 measures the amount of wear of the tire whose rubber index is to be calculated. As this device, the amount of wear testing devices that measure the amount of wear of a tire with the so-called Lambourne test described in Japanese Patent No. 3,277,155 and JP-A No. 2006-242697 can be used.

Next, processing that is executed by the CPU 18 of the tire rubber index calculating device 12 will be described with reference to the flowchart shown in FIG. 3. A program of the processing routine shown in FIG. 3 is stored beforehand in the hard disk 36, for example, and is executed as a result of the CPU 18 reading out the program from the hard disk 36.

Figure 3:
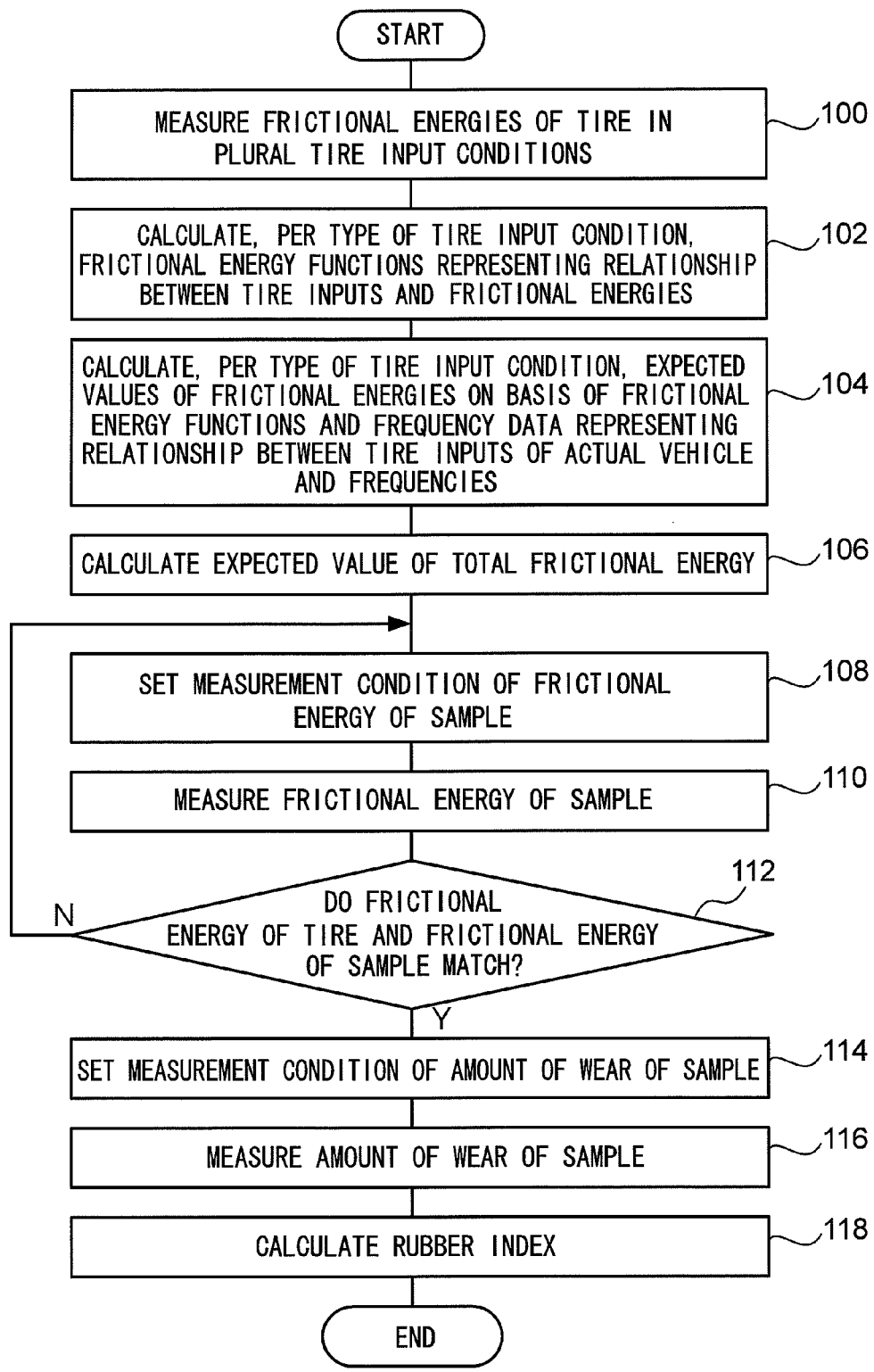
FIG. 3 is a flowchart showing a flow of rubber index calculation processing that is executed by a rubber index calculating device pertaining to a first embodiment.

First, in step 100 shown in FIG. 3, the rubber index calculating device 12 instructs the frictional energy measuring device 14, in which a tire whose rubber index is to be calculated has been set, to measure, in plural tire input conditions, the frictional energies of the tire whose rubber index is to be calculated. Examples of types of tire inputs include the drive force (front-and-rear force), the lateral force (left-and-right force), and the braking force that act on the tire, so the rubber index calculating device 12 sets plural tire input conditions in regard to each of these types of tire inputs, for example. In order to keep the description simple, a case where the drive force and the lateral force have been set as tire input conditions will be described below.

When the frictional energy measuring device 14 is instructed to measure by the rubber index calculating device 12, the frictional energy measuring device 14 measures the frictional energies of the tire in regard to each of the plural tire input conditions that have been instructed. Because of this, for example, frictional energies when plural different drive forces have been applied to the tire and frictional energies when plural different lateral forces have been applied to the tire are respectively measured by the frictional energy measuring device 14. The frictional energies that have been measured are outputted to the rubber index calculating device 12.

In step 102, the rubber index calculating device 12 calculates, per type of the tire input conditions, frictional energy functions representing the correspondence relationships between the tire inputs and the frictional energies. That is, the rubber index calculating device 12 calculates a frictional energy function f1 representing the correspondence relationship between the drive forces and the frictional energies on the basis of the frictional energies that were measured by applying the different plural drive forces to the tire. These frictional energy functions can be found using the method of least squares, for example. Likewise, the rubber index calculating device 12 calculates a frictional energy function f2 representing the correspondence relationship between the lateral forces and the frictional energies.

In step 104, the rubber index calculating device 12 calculates expected values of the frictional energies per type of the tire inputs on the basis of the frictional energy functions that were found in step 102 and frequency data representing the relationships between tire inputs that were measured when a vehicle equipped with the tire whose rubber index is to be calculated actually traveled a predetermined traveling course and their frequencies.

The frequency data are obtained as follows, for example. First, sensors that measure the drive force and the lateral force inputted to the tire are attached to the vehicle, the vehicle travels the above-described traveling course, and the sensors measure the drive force and the lateral force during travel. Then, on the basis of the data of the drive force and the lateral force that have been measured, the rubber index calculating device 12 determines the frequency of each input. Because of this, the frequency data representing that relationship between the drive force and lateral force that have been measured in an actual vehicle and the frequencies (%) of these are obtained. The frequency data that have been obtained are, for example, stored in the hard disk 36 beforehand.

Additionally, the rubber index calculating device 12 calculates, with the frictional energy function f1, each of the frictional energies corresponding to the data, of the frequency data, of the drive forces when the frictional energies of the tire were measured, multiplies each of the corresponding frequencies by the frictional energies that have been calculated, and adds these all together. Because of this, an expected value Ewd of the frictional energies of the drive forces is calculated. For example, in a case supposing that $Ewd_1, Ewd_2, \ldots Ewd_n$ (where n is the number of types of the frictional energies of the drive forces) represent the types of the frictional energies of the drive forces that have been measured and $h_1, h_2, \ldots h_n$ (where n is the number of types of the frictional energies of the drive forces) represent their frequencies, the expected value Ewd of the frictional energies of the drive forces is calculated by the following expression.

$$Ewd = Ewd_1 \times h_1 + Ewd_2 \times h_2 + \ldots Ewd_n \times h_n \quad (1)$$

Likewise in regard to the lateral forces also, the rubber index calculating device 12 finds the expected value Ewc of the frictional energies. That is, in a case supposing that $Ewc_1, Ewc_2, \ldots Ewc_n$ (where n is the number of types of the frictional energies of the lateral forces) represent the types of the frictional energies of the lateral forces that have been measured and $h_1, h_2, \ldots h_n$ (where n is the number of types of the frictional energies of the lateral forces) represent their frequencies, the expected value Ewc of the frictional energies of the lateral forces is calculated by the following expression.

$$Ewc = Ewc_1 \times h_1 + Ewc_2 \times h_2 + \ldots Ewc_n \times h_n \quad (2)$$

In step 106, the rubber index calculating device 12 calculates an expected value Ew of the total frictional energy by adding together the expected value Ewd of the frictional energies of the drive forces and the expected value Ewc of the frictional energies of the lateral forces that were found in step 104.

In step 108, the rubber index calculating device 12 establishes, on the basis of the expected value Ew of the frictional energy that was found in step 106, a measurement condition for measuring the frictional energy of the disc-shaped sample of the same material as the tread portion of the tire whose rubber index is to be calculated. In a case where the rubber index calculating device 12 has initially executed this step, the rubber index calculating device 12 uses the frictional energy functions f1 and f2 to find each of the drive force corresponding to the expected value Ewd of the frictional energies of the drive forces and the lateral force corresponding to the expected value Ewc of the frictional energies of the lateral forces that were found in step 104 and sets the drive force and lateral force that have been found as a measurement condition (sample input condition) for measuring the frictional energy of the sample.

In step 110, the rubber index calculating device 12 instructs the frictional energy measuring device 14 in which the sample has been set to measure the frictional energy of the sample in the measurement condition that was set in step 108. Because of this, the frictional energy measuring device 14 measures the frictional energy of the sample in the measurement condition that has been instructed by the rubber index calculating device 12. The measurement of the frictional energy of the sample is performed by measuring the shear force applied to the contact patch of the sample and the slippage and finding the frictional energy on the basis of these. The frictional energy that has been measured is outputted to the rubber index calculating device 12.

In step 112, the rubber index calculating device 12 judges whether or not the expected value Ew of the frictional energy of the tire that was found in step 106 and the frictional energy of the sample that was measured by the frictional energy measuring device 14 in step 110 match, and in a case where they do not match, the rubber index calculating device 12 returns to step 108, changes the measurement condition, and repeats the same processing as described above. Additionally, in a case where the expected value Ew of the frictional energy of the tire and the frictional energy of the sample match, the rubber index calculating device 12 moves to step 114. In this way, the rubber index calculating device 12 changes the measurement condition and repeats the processing in which it measures the frictional energy of the sample until the expected value Ew of the frictional energy of the tire and the frictional energy of the sample match.

In step 114, the rubber index calculating device 12 sets, as a measurement condition for measuring the amount of wear of the sample, the measurement condition in which the expected value Ew of the frictional energy of the tire and the frictional energy of the sample match.

In step 116, the rubber index calculating device 12 instructs the amount of wear measuring device 16 to measure the amount of wear in the measurement condition that was set in step 114—that is, the measurement condition (drive force and lateral force) in which the expected value Ew of the frictional energy of the tire and the frictional energy of the sample matched. Because of this, the amount of wear measuring device 16 measures an amount of wear m of the sample in the measurement condition that has been instructed by the rubber index calculating device 12. The amount of wear that has been measured is outputted to the rubber index calculating device 12.

In step 118, the rubber index calculating device 12 calculates a rubber index G on the basis of the expected value Ew of the frictional energy of the sample and the amount of wear m that have been found, outputs the calculation result to the monitor 32 and the hard disk 36, for example, and causes the calculation result to be displayed on the monitor 32 and stored in the hard disk 36. The rubber index G is found by the following expression.

$$G = m/Ew \qquad (3)$$

In this way, in the present embodiment, the rubber index calculating device 12 measures with the frictional energy measuring device 14 that measures the frictional energy of the sample on the basis of the shear force and the slippage of the tire contact patch, tailors the measurement condition of the sample in such a way that the frictional energy of the sample that has been measured matches the frictional energy of the tire, and calculates the rubber index on the basis of the amount of wear of the sample that has been measured in this measurement condition and the frictional energy of the sample. For this reason, compared to the case of calculating a frictional energy that has been averaged on the basis of the axial force like conventionally, the frictional energy can be measured precisely and the rubber index can be calculated precisely.

Second Embodiment

Next, a second embodiment of the present invention will be described. The same reference signs will be given to portions that are the same as those in the first embodiment, and detailed description thereof will be omitted.

In the first embodiment, the rubber index calculating device 12 calculated the rubber index after finding the frictional energy functions per type of the tire input conditions and finding the expected value of the total tire frictional energy, but in the present embodiment, a case where the rubber index calculating device 12 calculates rubber indexes in regard to each of the tire input conditions and calculates an expected value of the rubber index from these rubber indexes.

The rubber index calculating device pertaining to the present embodiment is the same as in the first embodiment, so description will be omitted.

Next, processing that is executed by the CPU 18 of the tire rubber index calculating device 12 will be described with reference to the flowchart shown in FIG. 4. A program of the processing routine shown in FIG. 4 is stored beforehand in the hard disk 36, for example, and is executed as a result of the CPU 18 reading out the program from the hard disk 36.

Figure 4:
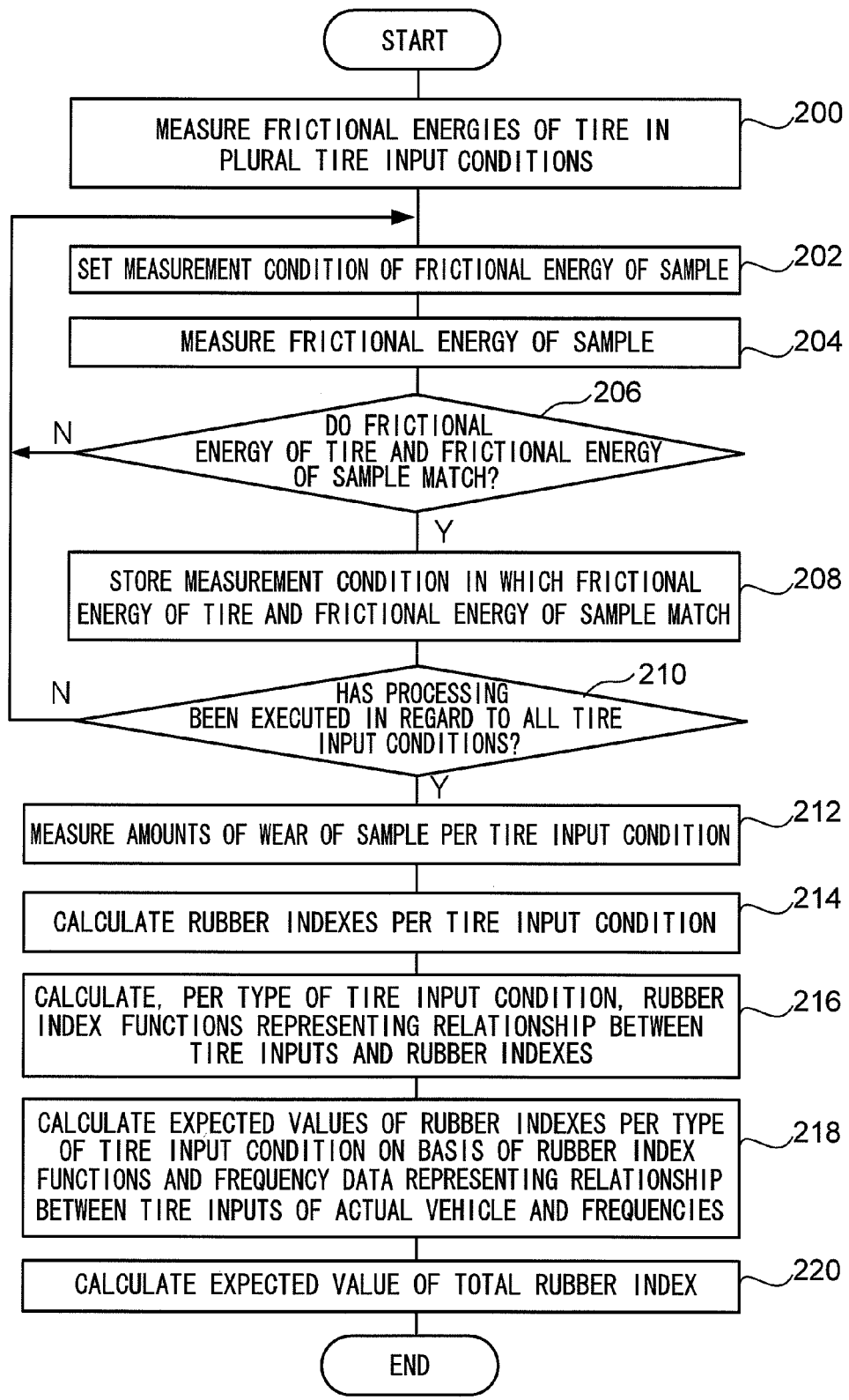
FIG. 4 is a flowchart showing a flow of rubber index calculation processing that is executed by the rubber index calculating device pertaining to a second embodiment.

First, in step 200 shown in FIG. 4, like in step 100 of FIG. 3, the rubber index calculating device 12 instructs the frictional energy measuring device 14, in which a tire whose rubber index is to be calculated has been set, to measure, in plural tire input conditions, the frictional energies of the tire whose rubber index is to be calculated.

Because of this, the frictional energy measuring device 14 measures the frictional energies of the tire in regard to each of the plural tire input conditions that have been instructed by the rubber index calculating device 12. Because of this, for example, frictional energies when plural different drive forces have been applied to the tire and frictional energies when plural different lateral forces have been applied to the tire are respectively measured by the frictional energy measuring device 14. The frictional energies that have been measured are outputted to the rubber index calculating device 12.

In step 202, the rubber index calculating device 12 sets, as a measurement condition for measuring the frictional energy of the sample, any of the tire input conditions of the plural tire input conditions in which the frictional energies were found in step 200.

In step 204, the rubber index calculating device 12 instructs the frictional energy measuring device 14 in which the sample has been set to measure the frictional energy of the sample in the measurement condition that was set in step 202. Because of this, the frictional energy measuring device 14 measures the frictional energy of the sample in the measurement condition that has been instructed by the rubber index calculating device 12. The frictional energy that has been measured is outputted to the rubber index calculating device 12.

In step 206, the rubber index calculating device 12 judges whether or not the frictional energy of the tire that was found in step 200 and the frictional energy of the sample that was measured by the frictional energy measuring device 14 in step 204 match, and in a case where they do not match, the rubber index calculating device 12 returns to step 202, changes the measurement condition, and repeats the same processing as described above. Additionally, in a case where the frictional energy of the tire and the frictional energy of the sample match, the rubber index calculating device 12 moves to step 208 and stores that measurement condition in the hard disk 36. In this way, the rubber index calculating device 12 changes the measurement condition and repeats the processing in which it measures the frictional energy of the sample until the frictional energy of the tire and the frictional energy of the sample match.

In step 210, the rubber index calculating device 12 judges whether or not it has executed the above-described processing of steps 202 to 208 in regard to all of the tire input conditions that were measured in step 200; in a case where the rubber index calculating device 12 has executed the processing, the rubber index calculating device 12 moves to step 212, and in a case where there is a tire input condition that the rubber index calculating device 12 has not yet executed, the rubber index calculating device 12 returns to step 202 and repeats the same processing as described above. Because of this, measurement conditions for measuring amounts of wear of the sample corresponding to each of the plural tire input conditions that were measured in step 200 are each set.

In step 212, the rubber index measuring device 12 instructs the amount of wear measuring device 16 to measure, in regard to each of the tire input conditions, each of the amounts of wear in the measurement conditions (drive force and lateral force) when the frictional energy of the tire and the frictional energy of the sample matched. Because of this, the amount of wear measuring device 16 measures each of the amounts of wear of the sample in each of the measurement conditions that have been instructed by the rubber index calculating device 12. The amounts of wear that have been measured are outputted to the rubber index calculating device 12.

In step 214, the rubber index calculating device 12 calculates, in regard to each of the tire input conditions, each of the rubber indexes on the basis of the frictional energies of the sample and the amounts of wear.

In step 216, the rubber index calculating device 12 calculates, per type of the tire input conditions, rubber index functions representing the correspondence relationships between the tire inputs and the rubber indexes on the basis of the rubber indexes per tire input condition that were found in step 214. That is, the rubber index calculating device 12 calculates a rubber index function f3 representing the correspondence relationship between the drive forces and the rubber indexes on the basis of the rubber indexes that were calculated in regard to the plural drive force tire input conditions. This rubber index function f3 can be found using the method of least squares, for example. Likewise, the rubber index calculating device 12 calculates a rubber index function f4 representing the correspondence relationship between the lateral forces and the rubber indexes. These rubber index functions can be found using the method of least squares, for example.

In step 218, the rubber index calculating device 12 calculates, per type of tire input condition, expected values of the rubber indexes on the basis of the rubber index functions per type of tire input condition that were found in step 216 and frequency data representing the relationships between tire inputs that were measured when a vehicle equipped with the tire whose rubber index is to be calculated actually traveled a predetermined traveling course and their frequencies.

That is, the rubber index calculating device 12 calculates, with the rubber index function f3, each of the rubber indexes corresponding to the data, of the frequency data, of the drive forces when the frictional energies of the tire were measured, multiplies the corresponding frequencies by the rubber indexes that have been calculated, and adds these all together. Because of this, an expected value Gd of the rubber indexes of the drive forces is calculated. For example, in a case supposing that $Gd_1, Gd_2, \ldots Gd_n$ (where n is the number of types of the rubber indexes of the drive forces) represent the types of the rubber indexes of the drive forces and $h_1, h_2, \ldots h_n$ (where n is the number of types of the rubber indexes of the drive forces) represent their frequencies, the expected value Gd of the rubber indexes of the drive forces is calculated by the following expression.

$$Gd = Gd_1 \times h_1 + Gd_2 \times h_2 + \ldots Gd_n \times h_n \qquad (4)$$

Likewise in regard to the lateral forces also, the rubber index calculating device 12 finds the expected value Gc of the rubber indexes. That is, in a case supposing that $Gc_1, Gc_2, \ldots Gc_n$ (where n is the number of types of the rubber indexes of the lateral forces) represent the types of the rubber indexes of the lateral forces and $h_1, h_2, \ldots h_n$ (where n is the number of types of the rubber indexes of the lateral forces) represent the frequencies thereof, the expected value Gc of the rubber indexes of the lateral forces is calculated by the following expression.

$$Gc = Gc_1 \times h_1 + Gc_2 \times h_2 + \ldots Gc_n \times h_n \qquad (5)$$

In step 220, the rubber index calculating device 12 calculates an expected value Gw of the total rubber index by adding together the expected value Gd of the rubber indexes of the drive forces and the expected value Gc of the rubber indexes of the lateral forces that were found in step 218.

In this way, in the present embodiment, the rubber index calculating device 12 measures with the frictional energy measuring device 14 that measures the frictional energy of the sample on the basis of the shear force and the slippage of the tire contact patch, tailors the measurement condition of the sample in such a way that the frictional energy of the sample that has been measured matches the frictional energy of the tire, and calculates the rubber index on the basis of the amount of wear of the sample that has been measured in this measurement condition and the frictional energy of the sample. For this reason, compared to the case of calculating a frictional energy that have been averaged on the basis of the axial force like conventionally, the frictional energy can be measured precisely and the rubber index can be calculated precisely.

Third Embodiment

Next, a third embodiment of the present invention will be described. The same reference signs will be given to portions that are the same as those in the first embodiment, and detailed description thereof will be omitted.

In the first embodiment, the rubber index calculating device 12 measured the frictional energy of the sample with the frictional energy measuring device 14, but in the present embodiment, a case where the rubber index calculating device 12 uses a sample model in which the sample is divided into plural elements and finds the frictional energy of the contact patch of the sample by a simulation using the finite element method (FEM) will be described.

The rubber index calculating device pertaining to the present embodiment is the same as in the first embodiment, so description will be omitted.

Figure 5:
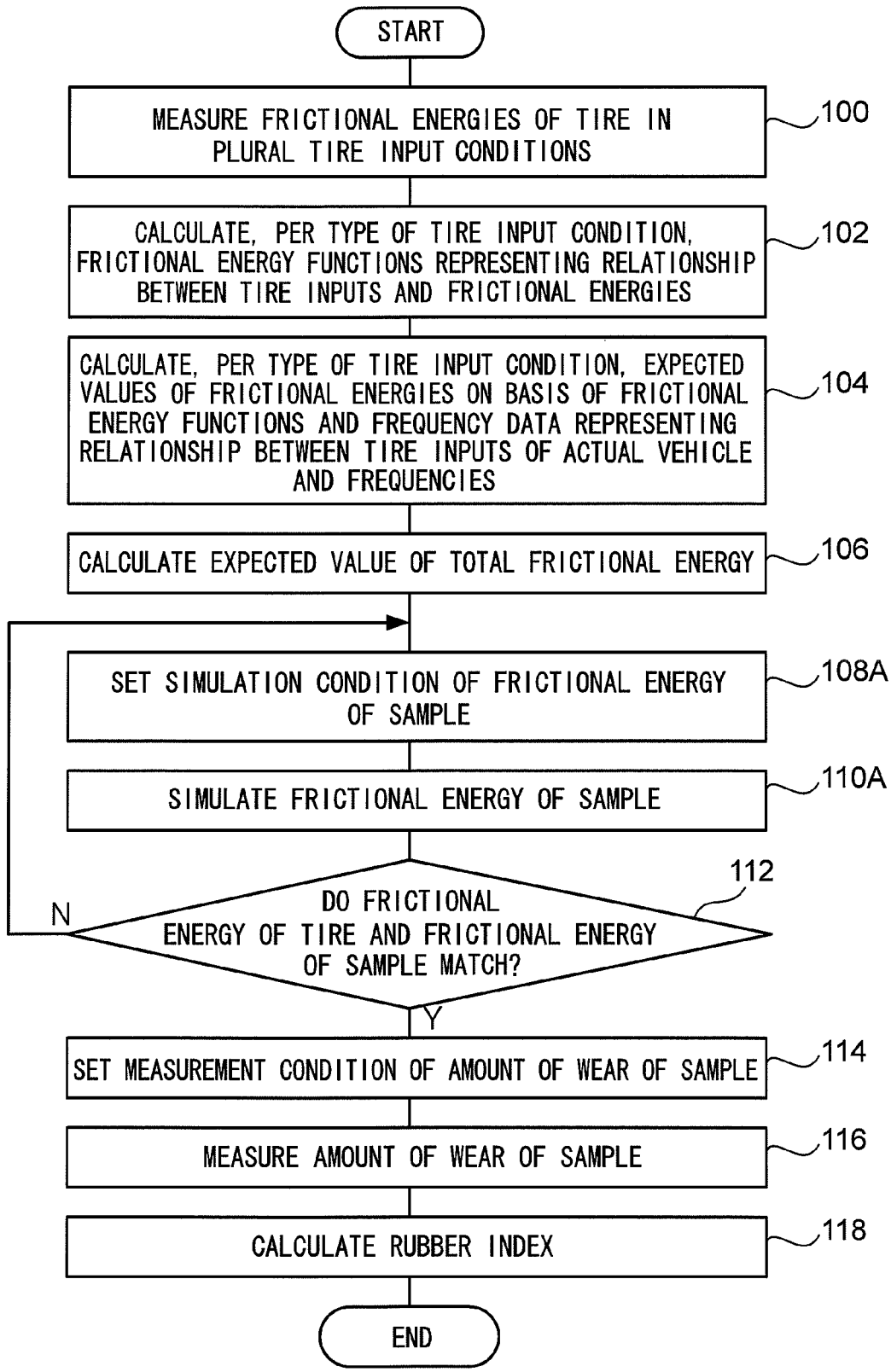
FIG. 5 is a flowchart showing a flow of rubber index calculation processing that is executed by the rubber index calculating device pertaining to a third embodiment.

Next, processing that is executed by the CPU 18 of the tire rubber index calculating device 12 will be described with reference to the flowchart shown in FIG. 5. A program of the processing routine shown in FIG. 5 is stored beforehand in the hard disk 36, for example, and is executed as a result of the CPU 18 reading out the program from the hard disk 36. Further, an "A" will be added to reference signs of steps of processing differing from the flowchart shown in FIG. 3, and in regard to the same processing, the same reference signs will be added thereto and detailed description thereof will be omitted.

Steps 100 to 106 are the same as the processing shown in FIG. 3, so description will be omitted.

In step 108A, the rubber index calculating device 12 finds, on the basis of the expected value Ew of the frictional energy that was found in step 106, a simulation condition for simulating the frictional energy of the disc-shaped sample of the same material as the tread portion of the tire whose rubber index is to be calculated. In a case where the rubber index calculating device 12 has initially executed this step, the rubber index calculating device 12 uses the frictional energy functions f1 and f2 to find each of the drive force corresponding to the expected value Ewd of the frictional energies of the drive forces and the lateral force corresponding to the expected value Ewc of the frictional energies of the lateral forces that were found in step 104 and sets the drive force and the lateral force that were found as a simulation conditions (sample input condition) for simulating the frictional energy of the sample.

In step 110A, the rubber index calculating device 12 simulates the frictional energy of the sample in the simulation condition that was set in step 108A. For example, the rubber index calculating device 12 creates a sample model in which the sample has been mesh-divided into plural elements and rolls and analyzes, with a publicly known technique using the finite element method, the sample model in the simulation condition that was set in step 108A to thereby find the shear force and the slippage of the contact patch of the sample. Additionally, the rubber index calculating device 12 calculates the frictional energy of the sample on the basis of the shear force and the slippage that were found.

Steps 112 to 118 are the same as the processing shown in FIG. 3 except that the frictional energies of the tire used in the processing are the frictional energies that were calculated by simulation, so description will be omitted.

In this way, in the present embodiment, the rubber index calculating device 12 calculates the frictional energy of the sample on the basis of the shear force and the slippage of the tire contact patch that were found by simulation, tailors the simulation condition of the sample in such a way that the frictional energy of the sample that has been calculated matches the frictional energy of the tire, and calculates the rubber index on the basis of the amount of wear of the sample that has been measured in this condition and the frictional energy of the sample. For this reason, compared to the case of calculating a frictional energy that has been averaged on the basis of the axial force like conventionally, the frictional energy can be measured precisely and the rubber index can be calculated precisely.

Fourth Embodiment

Next, a fourth embodiment of the present invention will be described. The same reference signs will be given to portions that are the same as those in the second embodiment, and detailed description thereof will be omitted.

In the second embodiment, the rubber index calculating device 12 measured the frictional energy of the sample with the frictional energy measuring device 14, but in the present embodiment, a case where the rubber index calculating device 12 uses a sample model in which the sample is divided into plural elements and finds the frictional energy of the contact patch of the sample by a simulation using the finite element method will be described.

The rubber index calculating device pertaining to the present embodiment is the same as in the first embodiment, so description will be omitted.

Figure 6:
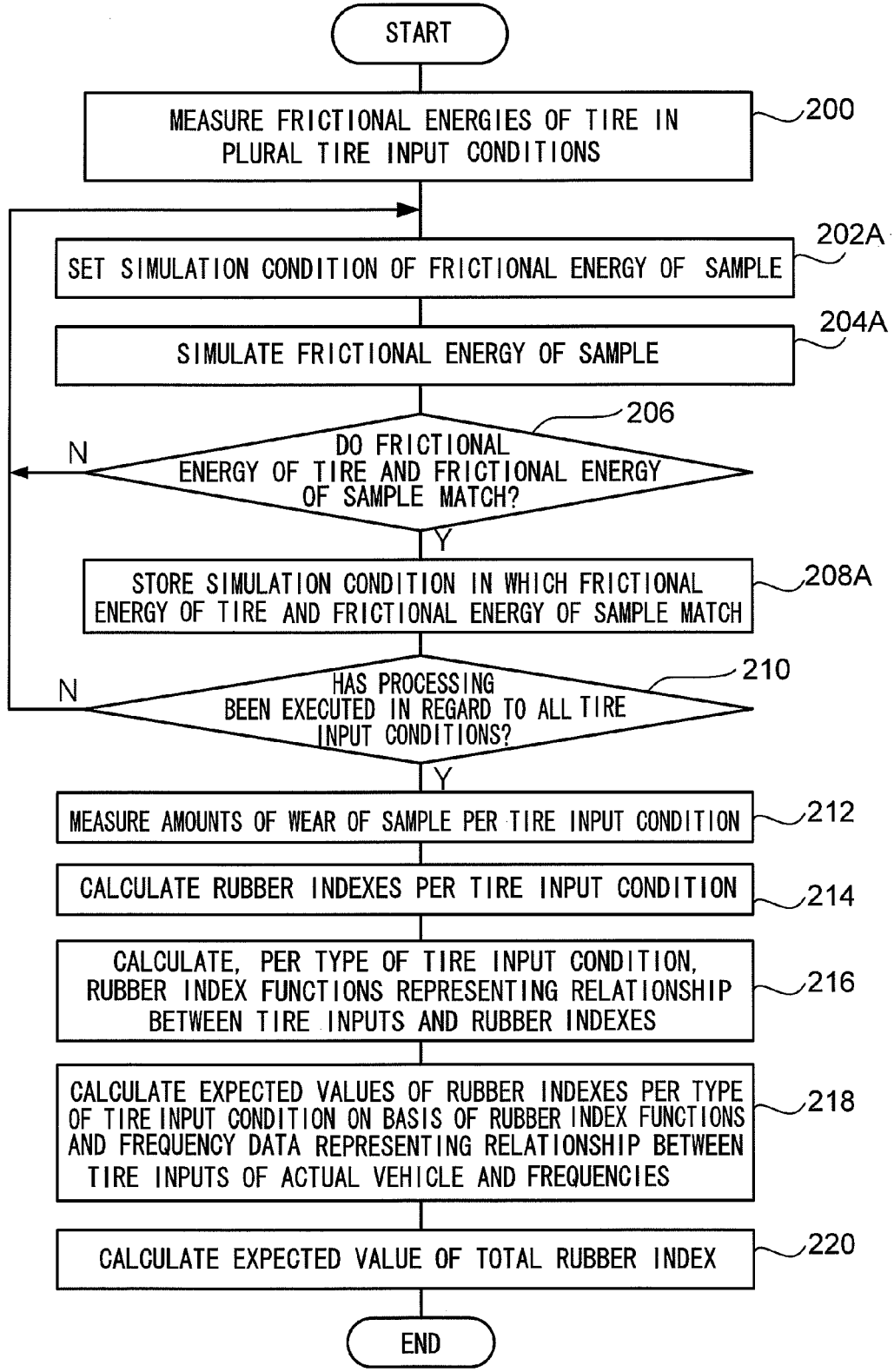
FIG. 6 is a flowchart showing a flow of rubber index calculation processing that is executed by the rubber index calculating device pertaining to a fourth embodiment.
Figure 7:
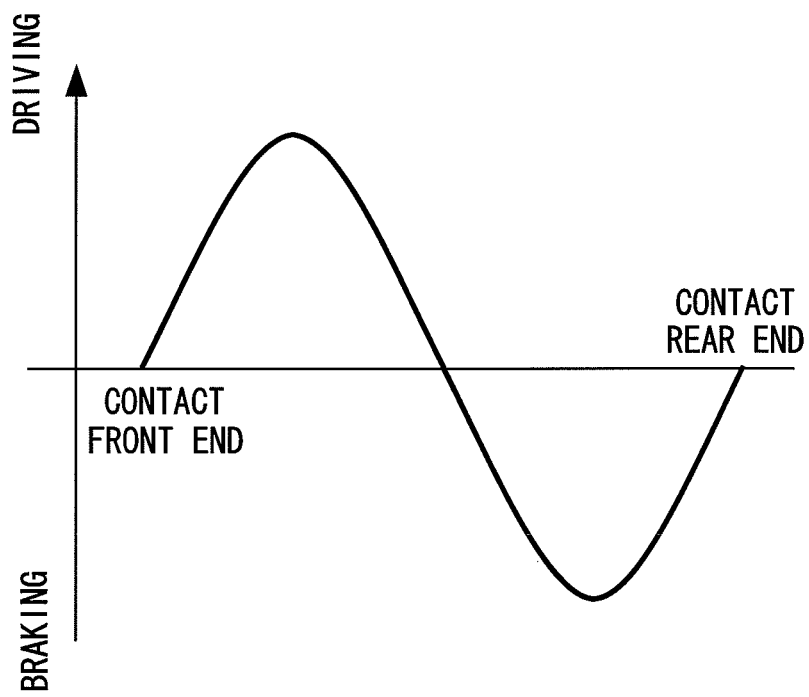
FIG. 7 is a diagram showing the relationship between a driving force and a braking force that are inputted from a contact front end to a contact rear end of a tire.
Figure 8:
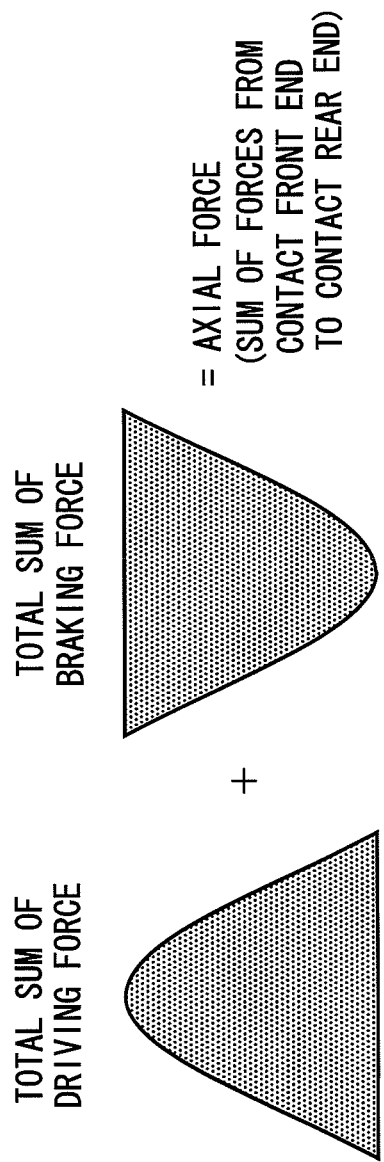
FIG. 8 is a conceptual diagram for describing the axial force of the tire.
Figure 9:
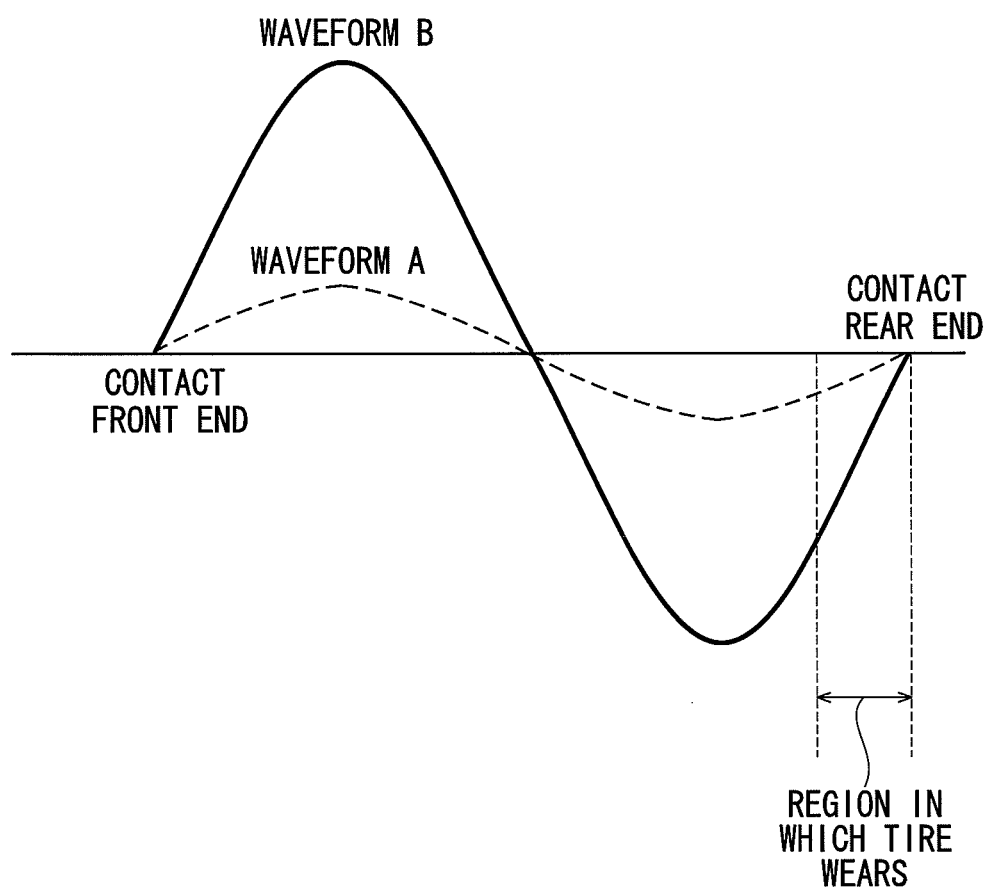
FIG. 9 is a diagram for describing a region in which the tire wears between the contact front end and the contact rear end of the tire.

Next, processing that is executed by the CPU 18 of the tire rubber index calculating device 12 will be described with reference to the flowchart shown in FIG. 6. A program of the processing routine shown in FIG. 6 is stored beforehand in the hard disk 36, for example, and is executed as a result of the CPU 18 reading out the program from the hard disk 36. Further, an "A" will be added to reference signs of steps of processing differing from the flowchart shown in FIG. 4, and in regard to the same processing, the same reference signs will be added thereto and detailed description thereof will be omitted.

Step 200 shown in FIG. 6 is the same as step 200 of FIG. 4, so description will be omitted.

In step 202A, the rubber index calculating device 12 sets, as a simulation condition for simulating the frictional energy of the sample, any of the tire input conditions of the plural tire input conditions in which the frictional energies were found in step 200.

In step 204A, like in step 108A of FIG. 5, the rubber index calculating device 12 calculates, by simulation, the frictional energy of the sample in the simulation condition that was set in step 202A.

In step 206, the rubber index calculating device 12 judges whether or not the frictional energy of the tire that was found in step 200 and the frictional energy of the sample that was calculated in step 204A match, and in a case where they do not match, the rubber index calculating device 12 returns to step 202A, changes the simulation condition, and repeats the same processing as described above. Additionally, in a case where the frictional energy of the tire and the frictional energy of the sample match, the rubber index calculating device 12 moves to step 208A and stores that simulation condition in the hard disk 36. In this way, the rubber index calculating device 12 changes the simulation condition and repeats the processing in which it simulates the frictional energy of the sample until the frictional energy of the tire and the frictional energy of the sample match.

In step 210, the rubber index calculating device 12 judges whether or not it has executed the above-described processing of steps 202A to 208A in regard to all the tire input conditions that were measured in step 200; in a case where the rubber index calculating device 12 has executed the processing, the rubber index calculating device 12 moves to step 212, and in a case where there is a tire input condition that the rubber index calculating device 12 has not yet executed, the rubber index calculating device 12 returns to step 202A and repeats the same processing as described above. Because of this, measurement conditions for measuring amounts of wear of the sample corresponding to each of the plural tire input conditions that were measured in step 200 are each set.

Steps 212 to 220 are the same as the processing shown in FIG. 4 except that the frictional energies of the tire used in the processing are the frictional energies that were calculated by simulation, so description will be omitted.

In this way, in the present embodiment, the rubber index calculating system calculates the frictional energy of the sample by simulation on the basis of the shear force and the slippage of the tire contact patch, tailors the simulation condition of the sample in such a way that the frictional energy of the sample that has been calculated matches the frictional energy of the tire, and calculates the rubber index on the basis of the amount of wear of the sample that has been measured in this simulation condition and the frictional energy of the sample. For this reason, compared to the case of calculating a frictional energy that has been averaged on the basis of the axial force like conventionally, the frictional energy can be measured precisely and the rubber index can be calculated precisely.

EXAMPLES

Next, examples of the present invention will be described.

Figure 10:
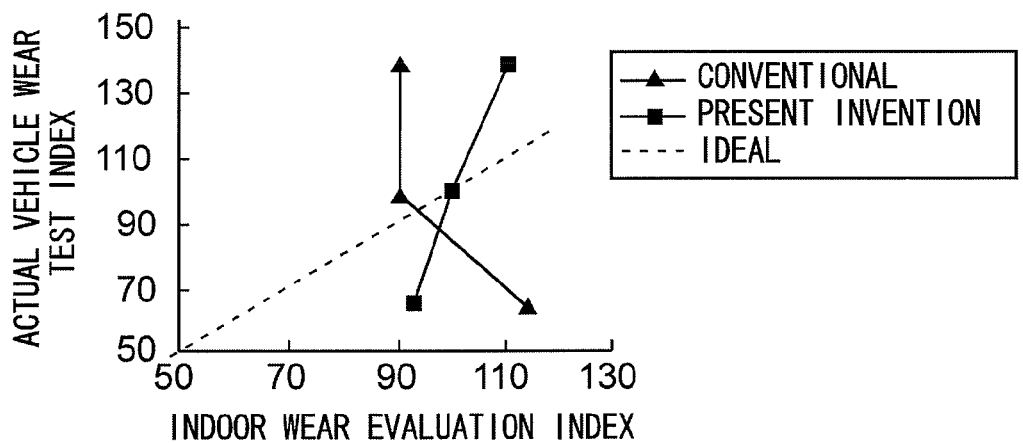
FIG. 10 is a graph showing the relationship between an indoor wear evaluation index, which are evaluation values relating to tire wear that were found from the results of a simulation described in the first embodiment and the results of a conventional simulation, and an actual vehicle wear test index, which are evaluation values relating to tire wear that were found from the amounts of wear and so forth of tires measured after traveling on an actual vehicle.

FIG. 10 shows the relationship between an indoor wear evaluation index, which are evaluation values relating to tire wear that were found from the results of the simulation described in the first embodiment and the results of a conventional simulation, and an actual vehicle wear test index, which are evaluation values relating to tire wear that were found from the amounts of wear of tires measured after traveling on an actual vehicle.

The vehicle that was used in the traveling test by the actual vehicle was a truck whose front wheels had one steering axle and whose rear wheels had two driving axles; the vehicle traveled in conditions in which the tire size was 11R22.5, the internal pressure was 900 kPa, the load was 25 kN, and the traveling speed was 0 to 100 km/h, and the amount of wear and so forth were measured. The actual vehicle wear test indexes were found from these measurement results.

Each of the simulations was performed in the same conditions as those in the traveling test by the actual vehicle and according to the conventional method and the method described in the first embodiment, and on the basis of those results, the indoor wear evaluation indexes relating to tire wear were each found. The simulation with the conventional method is a method that finds the amount of wear and so forth while keeping the slip ratio of the tire constant.

As indicated by the dashed line in FIG. 10, the ideal is for the indoor wear evaluation index and the actual vehicle wear test index to match, but in the conventional simulation results, the slope is the opposite of the slope in the ideal case. In contrast, in the simulation results pertaining to the first embodiment of the present invention, the slope is the same as in the ideal case.

Figure 11:
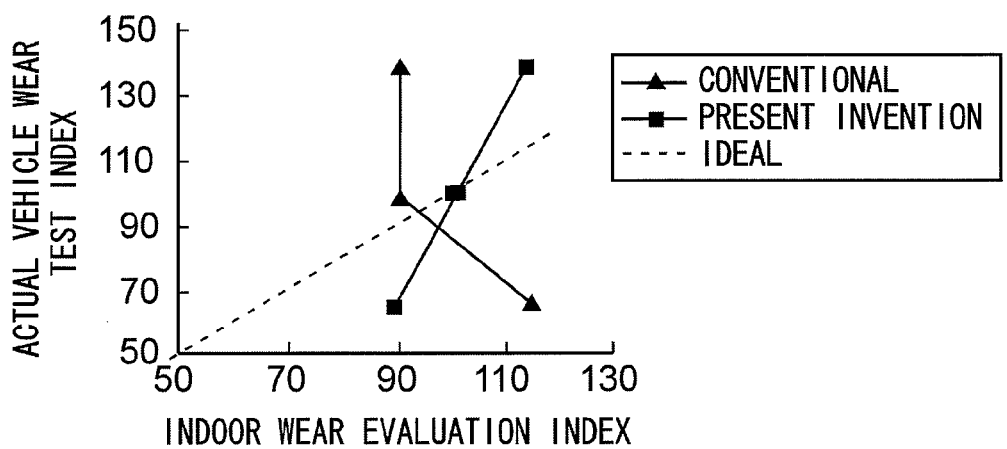
FIG. 11 is a graph showing the relationship between an indoor wear evaluation index, which are evaluation values relating to tire wear that were found from the results of a simulation described in the second embodiment and the results of a conventional simulation, and an actual vehicle wear test index, which are evaluation values relating to tire wear that were found from the amount of wear and so forth of tires measured after traveling on an actual vehicle.
Figure 12:
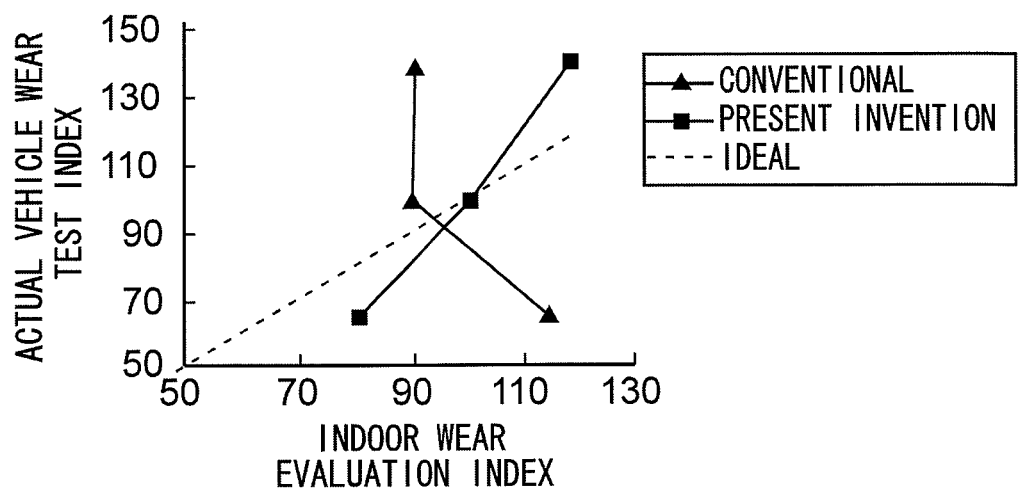
FIG. 12 is a graph showing the relationship between an indoor wear evaluation index, which are evaluation values relating to tire wear that were found from the results of a simulation described in the third embodiment and the results of a conventional simulation, and an actual vehicle wear test index, which are evaluation values relating to tire wear that were found from the amounts of wear and so forth of tires measured after traveling on an actual vehicle.
Figure 13:
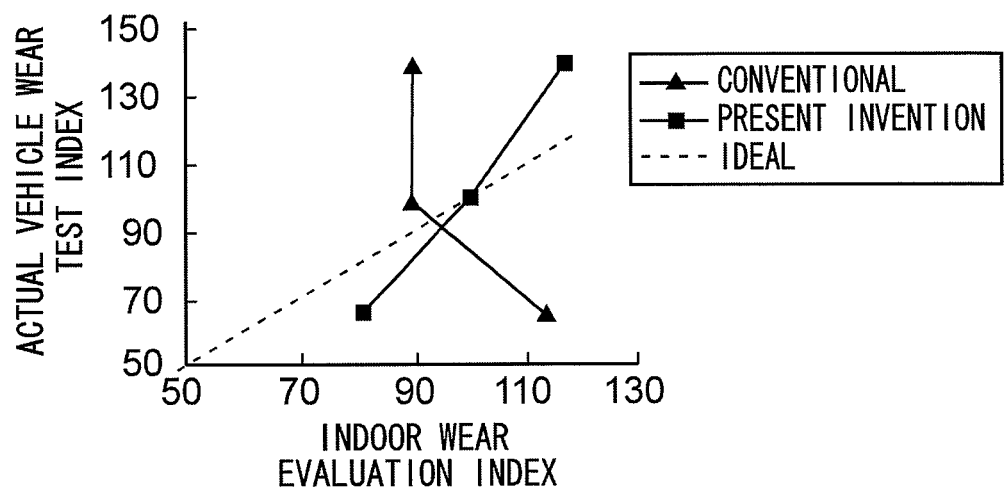
FIG. 13 is a graph showing the relationship between an indoor wear evaluation index, which are evaluation values relating to tire wear that were found from the results of a simulation described in the fourth embodiment and the results of a conventional simulation, and an actual vehicle wear test index, which are evaluation values relating to tire wear that were found from the amounts of wear and so forth of tires measured after traveling on an actual vehicle.

Likewise, FIG. 11 to FIG. 13 each show the relationship between an indoor wear evaluation index, which are evaluation values relating to tire wear that were found from the results of the simulations described in the second to fourth embodiments and the results of a conventional simulation, and an actual vehicle wear test index, which are evaluation values relating to tire wear that were found from the amounts of wear of tires after traveling on an actual vehicle.

As shown in FIG. 11 to FIG. 13, in regard to the simulation results pertaining to the second to fourth embodiments also, the slope is the same as in the ideal case.

In this way, it was understood that, with the simulations pertaining to the first to fourth embodiments of the present invention, the relationship between the indoor wear evaluation index and the actual vehicle wear test index can be brought closer to the ideal state and, as a result, the rubber index can be precisely calculated.

The invention claimed is:

1. A tire rubber index calculating method comprising:
   a tire frictional energy measuring step of measuring, by a processor and a frictional energy measuring device comprising a force applying device, an image capturing device and a shear force measuring device, tire frictional energies of a tire in plural tire input conditions applied to the tire, the tire frictional energy measuring step including:
      applying, by the force applying device, the plural tire input conditions to the tire;
      capturing, by the image capturing device, an image of the contact patch of the tire and measuring a slippage of the tire contact patch from the image;
      measuring, by the shear force measuring device, a shear force applied to the tire by the force applying device; and
      calculating, by the processor, tire frictional energies of a tire on the basis of the shear force and the slippage of the tire contact patch and storing the tire frictional energies in a memory;
   a setting step including:
      setting, by the processor, sample input conditions for a sample of the same material as the tire on the basis of the tire frictional energies in the tire input conditions that were measured;
      obtaining, by the frictional energy measuring device, sample frictional energies of the sample in the sample input conditions;
      storing, by the processor, the sample frictional energies in the memory; and
      setting, by the processor, measurement conditions for measuring sample amounts of wear of the sample on the basis of the tire frictional energies in the tire input conditions that were measured and the sample frictional energies that were obtained for the sample input conditions;
   a sample amount of wear measuring step of measuring, by a Lambourne testing device, the sample amounts of wear of the sample in the measurement conditions that were set and storing the sample amounts of wear that were measured in the memory; and
   a rubber index calculating step of calculating, by the processor, a rubber index of the tire on the basis of the sample frictional energies and the sample amounts of wear that were measured, wherein
   the setting step further includes:
      a step of calculating, by the processor, per type of the tire input conditions, frictional energy functions representing the correspondence relationships between the tire input conditions and the tire frictional energies,
      a step of calculating, by the processor, expected values of the tire frictional energies on the basis of frequency data representing the relationships between tire inputs that were measured in actual vehicle travel using the tire and the frequencies of the tire inputs and the frictional energy functions per type of the tire input conditions, a sample input condition setting step of setting, by the processor, a sample input condition applied to the sample for measuring, by the frictional energy measuring device, the sample frictional energy of the sample, a sample frictional energy measuring step of repeatedly measuring, by the frictional energy measuring device, the sample frictional energy of the sample in the sample input condition that was set and measuring the sample frictional energy while changing the sample input condition until the sample frictional energy that has been measured matches the expected value of the tire frictional energy, and a sample amount of wear measurement condition setting step of setting, by the processor, as a measurement condition for measuring the sample amount of wear, the sample input condition in which the sample frictional energy that was measured matches the expected value of the tire frictional energy, and wherein the sample amount of wear measuring step comprises measuring, by the Lambourne testing device, the sample amount of wear of the sample in the measurement condition that was set in the sample amount of wear measurement condition setting step.

2. A tire rubber index calculating method comprising:

a tire frictional energy measuring step of measuring, by a processor and a frictional energy measuring device comprising a force applying device, an image capturing device and a shear force measuring device, tire frictional energies of a tire in plural tire input conditions applied to the tire, the tire frictional energy measuring step including:

applying, by the force applying device, the plural tire input conditions to the tire;

capturing, by the image capturing device, an image of the contact patch of the tire and measuring a slippage of the tire contact patch from the image;

measuring, by the shear force measuring device, a shear force applied to the tire by the force applying device;

calculating, by the processor, tire frictional energies of a tire on the basis of the shear force and the slippage of the tire contact patch and storing the tire frictional energies in a memory;

a setting step including:

setting, by the processor, sample input conditions for a sample of the same material as the tire on the basis of the tire frictional energies in the tire input conditions that were measured;

obtaining, by the frictional energy measuring device, sample frictional energies of the sample in the sample input conditions;

storing, by the processor, the sample frictional energies in the memory; and setting, by the processor, measurement conditions for measuring sample amounts of wear of the sample on the basis of the tire frictional energies in the tire input conditions that were measured and the sample frictional energies that were obtained for the sample input conditions;

a sample amount of wear measuring step of measuring, by a Lambourne testing device, the sample amounts of wear of the sample in the measurement conditions that were set and storing the sample amounts of wear that were measured in the memory; and a rubber index calculating step of calculating, by the processor, a rubber index of the tire on the basis of the sample frictional energies and the sample amounts of wear that were measured, wherein the setting step includes in regard to each of the plural tire input conditions, a sample input condition setting step of setting, by the processor, a sample input condition applied to the sample for measuring, by the frictional energy measuring device, the sample frictional energy of the sample, a sample frictional energy measuring step of repeatedly measuring, by the frictional energy measuring device, the sample frictional energy of the sample in the sample input condition that was set and measuring the sample frictional energy while changing the sample input condition until the sample frictional energy that has been measured matches the tire frictional energy that was measured in the corresponding tire input condition, and a sample amount of wear measurement condition setting step of setting, by the processor, as a measurement condition for measuring the sample amount of wear, the sample input condition in which the sample frictional energy that was measured matches the tire frictional energy that was measured in the corresponding tire input condition, wherein the sample amount of wear measuring step comprises measuring, by the Lambourne testing device, the sample amounts of wear of the sample in the measurement conditions that were set in the sample amount of wear measurement condition setting step in regard to each of the plural tire input conditions, and the rubber index calculating step includes a step of calculating, by the processor, rubber indexes on the basis of the frictional energies and the sample amounts of wear in regard to each of the plural tire input conditions, a step of calculating, by the processor, per type of the tire input conditions, rubber index functions representing the correspondence relationships between the tire input conditions and the rubber indexes of the tire on the basis of the rubber indexes that were calculated in regard to each of the plural tire input conditions, and a step of calculating, by the processor, expected values of the rubber indexes on the basis of frequency data representing the relationships between tire inputs that were measured in actual vehicle travel using the tire and the frequencies of those tire inputs and the rubber index functions per type of the tire input conditions.

3. A tire rubber index calculating method comprising:

a tire frictional energy measuring step of measuring, by a processor and a frictional energy measuring device comprising a force applying device, an image capturing device and a shear force measuring device, tire frictional energies of a tire in plural tire input conditions applied to the tire, the tire frictional energy measuring step including:

applying, by the force applying device, the plural tire input conditions to the tire;

capturing, by the image capturing device, an image of the contact patch of the tire and measuring a slippage of the tire contact patch from the image;

measuring, by the shear force measuring device, a shear force applied to the tire by the force applying device; and calculating, by the processor, tire frictional energies of a tire on the basis of the shear force and the slippage of the tire contact patch and storing the tire frictional energies in a memory:

a setting step including:

setting, by the processor, sample input conditions for a sample of the same material as the tire on the basis of the tire frictional energies in the tire input conditions that were measured;

obtaining, by the frictional energy measuring device, sample frictional energies of the sample in the sample input conditions;

storing, by the processor, the sample frictional energies in the memory; and setting, by the processor, measurement conditions for measuring sample amounts of wear of the sample on the basis of the tire frictional energies in the tire input conditions that were measured and the sample frictional energies that were obtained for the sample input conditions;

a sample amount of wear measuring step of measuring, by a Lambourne testing device, the sample amounts of wear of the sample in the measurement conditions that were set and storing the sample amounts of wear that were measured in the memory; and a rubber index calculating step of calculating, by the processor, a rubber index of the tire on the basis of the sample frictional energies and the sample amounts of wear that were measured, wherein the setting step further includes a step of calculating, by the processor, per type of the tire input conditions, frictional energy functions representing the correspondence relationships between the tire input conditions and the tire frictional energies, a step of calculating, by the processor, expected values of the tire frictional energies on the basis of frequency data representing the relationships between tire inputs that were measured in actual vehicle travel using the tire and the frequencies of those tire inputs and the frictional energy functions per type of the tire input conditions, a sample input condition setting step of setting, by the processor, a sample input condition applied to the sample for computing the sample frictional energy of the sample on the basis of a sample model of the sample, a sample frictional energy computing step of repeatedly computing, by the processor, the sample frictional energy of the sample in the sample input condition that was set and computing the sample frictional energy while changing the sample input condition until the sample frictional energy that has been computed matches the expected value of the tire frictional energy, and a sample amount of wear measurement condition setting step of setting, by the processor, as a measurement condition for measuring the sample amount of wear, the sample input condition in which the sample frictional energy that was computed matches the expected value of the tire frictional energy, wherein the sample amount of wear measuring step comprises measuring, by the Lambourne testing device, the sample amount of wear of the sample in the measurement condition that was set in the sample amount of wear measurement condition setting step.

4. A tire rubber index calculating method comprising:

a tire frictional energy measuring step of measuring, by a processor and a frictional energy measuring device comprising a force applying device, an image capturing device and a shear force measuring device, tire frictional energies of a tire in plural tire input conditions applied to the tire, the tire frictional energy measuring step including:

applying, by the force applying device, the plural tire input conditions to the tire;

capturing, by the image capturing device, an image of the contact patch of the tire and measuring a slippage of the tire contact patch from the image;

measuring, by the shear force measuring device, a shear force applied to the tire by the force applying device; and calculating, by the processor, tire frictional energies of a tire on the basis of the shear force and the slippage of the tire contact patch and storing the tire frictional energies in a memory;

a setting step including:

setting, by the processor, sample input conditions for a sample of the same material as the tire on the basis of the tire frictional energies in the tire input conditions that were measured;

obtaining, by the frictional energy measuring device, sample frictional energies of the sample in the sample input conditions;

storing, by the processor, the sample frictional energies in the memory; and setting, by the processor, measurement conditions for measuring sample amounts of wear of the sample on the basis of the tire frictional energies in the tire input conditions that were measured and the sample frictional energies that were obtained for the sample input conditions;

a sample amount of wear measuring step of measuring, by a Lambourne testing device, the sample amounts of wear of the sample in the measurement conditions that were set and storing the sample amounts of wear that were measured in the memory; and a rubber index calculating step of calculating, by the processor, a rubber index of the tire on the basis of the sample frictional energies and the sample amounts of wear that were measured, wherein the setting step includes in regard to each of the plural tire input conditions, a sample input condition setting step of setting, by the processor, a sample input condition applied to the sample for computing the sample frictional energy of the sample on the basis of a sample model of the sample, a sample frictional energy computing step of repeatedly computing, by the processor, the sample frictional energy of the sample in the sample input condition that was set and computing the sample frictional energy while changing the sample input condition until the sample frictional energy that has been computed matches the tire frictional energy that was measured in the corresponding tire input condition, and a sample amount of wear measurement condition setting step of setting, by the processor, as a measurement condition for measuring the sample amount of wear, the sample input condition in which the sample frictional energy that was computed matches the tire frictional energy that was measured in the corresponding tire input condition, wherein, the sample amount of wear measuring step comprises measuring, by the Lambourne testing device, the sample amounts of wear of the sample in the measurement conditions that were set in the sample amount of wear measurement condition setting step in regard to each of the plural tire input conditions, and the rubber index calculating step includes
- a step of calculating, by the processor, rubber indexes on the basis of the frictional energies and the sample amounts of wear in regard to each of the plural tire input conditions,
- a step of calculating, by the processor, per type of the tire input conditions, rubber index functions representing the correspondence relationships between the tire input conditions and the rubber indexes of the tire on the basis of the rubber indexes that were calculated in regard to each of the plural tire input conditions, and
- a step of calculating, by the processor, expected values of the rubber indexes on the basis of frequency data representing the relationships between tire inputs that were measured in actual vehicle travel using the tire and the frequencies of those tire inputs and the rubber index functions per type of the tire input conditions.

5. A tire rubber index calculating device comprising:
a processor;
a tire frictional energy measuring device including a force applying device, an image capturing device and a shear force measuring device; and
a Lambourne testing device, wherein
the processor is configured to:
- instruct the tire frictional energy measuring device to apply, by the force applying device, the plural tire input conditions to the tire;
- instruct the tire frictional energy measuring device to capture, by the image capturing device, an image of the contact patch of the tire and to measure a slippage of the tire contact patch from the image;
- instruct the tire frictional energy measuring device to measure, by the shear force measuring device, a shear force applied to the tire by the force applying device;
- calculate tire frictional energies in the plural tire input conditions applied to the tire on the basis of the shear force and the slippage of the tire contact patch;
- set sample input conditions for a sample of the same material as the tire on the basis of the tire frictional energies in the tire input conditions that were measured,
- instruct the tire frictional energy measuring device to obtain sample frictional energies of the sample in the sample input conditions;
- set measurement conditions for measuring sample amounts of wear of the sample on the basis of the tire frictional energies in the tire input conditions that were measured and the sample frictional energies that were obtained in the sample input conditions;
- instruct the Lambourne testing device to measure the sample amounts of wear of the sample in the measurement conditions that were set; and
- calculate a rubber index of the tire on the basis of the sample frictional energies and the sample amounts of wear that were measured, wherein the processor is further configured to:
- calculate per type of the tire input conditions, frictional energy functions representing the correspondence relationships between the tire input conditions and the tire frictional energies,
- calculate expected values of the tire frictional energies on the basis of frequency data representing the relationships between tire inputs that were measured in actual vehicle travel using the tire and the frequencies of the tire inputs and the frictional energy functions per type of the tire input conditions,
- set a sample input condition applied to the sample for measuring, by the frictional energy measuring device, the sample frictional energy of the sample,
- instruct the frictional energy measuring device to repeatedly measure the sample frictional energy of the sample in the sample input condition that was set and measure the sample frictional energy while changing the sample input condition until the sample frictional energy that has been measured matches the expected value of the tire frictional energy, and
- set as a measurement condition for measuring the sample amount of wear, the sample input condition in which the sample frictional energy that was measured matches the expected value of the tire frictional energy, and wherein the Lambourne testing device is configured to measure the sample amount of wear of the sample in the measurement condition that was set in setting the sample amount of wear measurement condition.

6. A non-transitory computer-readable storage medium storing a tire rubber index calculating program for causing a computer comprising a processor and a memory to execute processing comprising:
a tire frictional energy measuring step of instructing a frictional energy measuring device comprising a force applying device, an image capturing device and a shear force measuring device, to measure tire frictional energies of a tire in plural tire input conditions applied to the tire, the tire frictional energy measuring step including:
- instructing the tire frictional energy measuring device to apply, by the force applying device, the plural tire input conditions to the tire;
- instructing the tire frictional energy measuring device to capture, by the image capturing device, an image of the contact patch of the tire and to measure a slippage of the tire contact patch from the image;
- instructing the tire frictional energy measuring device to measure, by the shear force measuring device, a shear force applied to the tire by the force applying device; and
- calculating tire frictional energies of the tire on the basis of the shear force and the slippage of the tire contact patch and storing the tire frictional energies in the memory;

a setting step including:
- setting sample input conditions for a sample of the same material as the tire on the basis of the tire frictional energies in the tire input conditions that were measured;
- instructing the frictional energy measuring device to obtain sample frictional energies of the sample;
- storing the sample frictional energies; and
- setting measurement conditions for measuring sample amounts of wear of the sample on the basis of the tire frictional energies in the tire input conditions that were measured and the sample frictional energies that were obtained in the sample input conditions;

a sample amount of wear measuring step of instructing a Lambourne testing device to measure the sample amounts of wear of the sample in the measurement conditions that were set; and a rubber index calculating step of calculating a rubber index of the tire on the basis of the sample frictional energies and the sample amounts of wear that were measured, wherein the setting step further includes:
- a step of calculating, by the processor, per type of the tire input conditions, frictional energy functions representing the correspondence relationships between the tire input conditions and the tire frictional energies,
- a step of calculating, by the processor, expected values of the tire frictional energies on the basis of frequency data representing the relationships between tire inputs that were measured in actual vehicle travel using the tire and the frequencies of the tire inputs and the frictional energy functions per type of the tire input conditions,
- a sample input condition setting step of setting, by the processor, a sample input condition applied to the sample for measuring, by the frictional energy measuring device, the sample frictional energy of the sample,
- a sample frictional energy measuring step of repeatedly measuring, by the frictional energy measuring device, the sample frictional energy of the sample in the sample input condition that was set and measuring the sample frictional energy while changing the sample input condition until the sample frictional energy that has been measured matches the expected value of the tire frictional energy, and
- a sample amount of wear measurement condition setting step of setting, by the processor, as a measurement condition for measuring the sample amount of wear, the sample input condition in which the sample frictional energy that was measured matches the expected value of the tire frictional energy, and wherein the sample amount of wear measuring step comprises measuring, by the Lambourne testing device, the sample amount of wear of the sample in the measurement condition that was set in the sample amount of wear measurement condition setting step.

* * * * *